United States Patent
Smith et al.

(10) Patent No.: US 11,773,067 B2
(45) Date of Patent: Oct. 3, 2023

(54) (TRIFLUOROMETHYL)PYRIMIDINE-2-AMINE COMPOUNDS

(71) Applicant: Eli Lilly and Company, Indianapolis, IN (US)

(72) Inventors: Daryl Lynn Smith, Fishers, IN (US); Leonard Larry Winneroski, Jr., Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/872,185

(22) Filed: Jul. 25, 2022

(65) Prior Publication Data
US 2022/0372003 A1    Nov. 24, 2022

Related U.S. Application Data

(63) Continuation of application No. 17/245,453, filed on Apr. 30, 2021, now Pat. No. 11,414,389.

(60) Provisional application No. 63/021,806, filed on May 8, 2020.

(51) Int. Cl.
C07D 239/47    (2006.01)
A61K 31/505    (2006.01)

(52) U.S. Cl.
CPC .......... *C07D 239/47* (2013.01); *A61K 31/505* (2013.01)

(58) Field of Classification Search
CPC .......................... C07D 239/47; A61K 31/505
See application file for complete search history.

(56) References Cited

U.S. PATENT DOCUMENTS

| | | | |
|---|---|---|---|
| 3,637,697 A * | 1/1972 | Anthony et al. | C07D 239/50 544/323 |
| 5,100,459 A | 3/1992 | Mayer et al. | |
| 6,326,368 B1 | 12/2001 | Chorvat et al. | |
| 11,414,389 B2 * | 8/2022 | Smith | A61P 25/04 |

FOREIGN PATENT DOCUMENTS

| | | |
|---|---|---|
| CA | 2248290 | 9/1998 |
| WO | 02/18374 A1 | 3/2002 |
| WO | 2008/052072 A2 | 5/2008 |
| WO | 2011/022440 A2 | 2/2011 |
| WO | 2014/121055 A2 | 8/2014 |

OTHER PUBLICATIONS

PubChem CID 72183404 (2013).*
PubChem SID 375376578 (2018).*
Wangdong, W., et al., "Discovery and Characterization of 2-(Cyclopropanesulfonamido)-N-(2-ethoxyphenyl)benzamide, ML382: a Potent and Selective Positive Allosteric Modulator of MrgX1," ChemMedChem, vol. 10(1), 57-61 (2015).
Aurora Chemical Catalog; online.aurorafinechemicals.com; accessed Mar. 16, 2021; supplemental information included, STN CAS# entry dates of 2015 and 2016.

* cited by examiner

*Primary Examiner* — Deepak R Rao
(74) *Attorney, Agent, or Firm* — Robert D. Shereda

(57) ABSTRACT

The present invention provides a compound of Formula I:

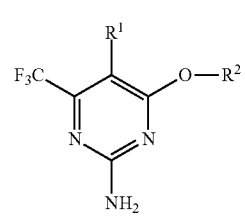

Formula I wherein $R^1$ is hydrogen or methyl; and
$R^2$ is:

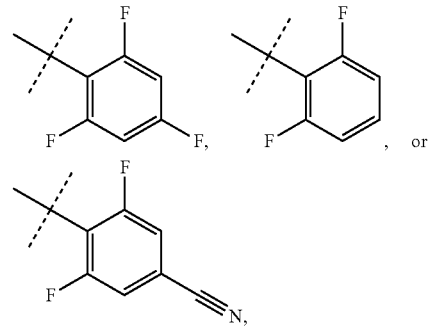

or a pharmaceutically acceptable salt thereof, useful for treating pain, including chronic pain, chronic lower back pain, diabetic peripheral neuropathic pain, and osteoarthritis pain.

5 Claims, No Drawings

(TRIFLUOROMETHYL)PYRIMIDINE-2-AMINE COMPOUNDS

The present invention relates to compounds that are potentiators of the hMrgX1 receptor, to pharmaceutical compositions comprising the compounds, to methods of using the compounds to treat pain, and to intermediates and processes useful in the synthesis of the compounds.

It is estimated that about 20% of adults in the United States alone suffer from chronic pain. Chronic pain is one of the most common reasons adults seek medical care and is linked to restrictions in mobility and daily activities. Unfortunately, chronic pain is often refractory to current therapies and many analgesics are associated with dose-limiting adverse events or serious risk of addiction and abuse which can be substantial barriers to their use in treating chronic pain. Thus, there is an unmet need for new chronic pain therapies, particularly treatments that have such adverse effects reduced or effectively eliminated.

U.S. Pat. No. 6,326,368 B1 discloses certain 2-aryloxy- and 2-arylthiosubstituted pyrimidines and triazines and derivatives thereof as corticotropin releasing factor (CRF) receptor antagonists useful in treating various disorders, such as depression, anxiety, drug addiction, and inflammatory disorders. U.S. Pat. No. 5,100,459 discloses certain substituted sulfonylureas and intermediates thereof. W. Wangdong, et. al., *Chem Med Chem*, vol 10(1), 57-61 (2015) disclose 2-(cyclopropanesulfonamido)-N-(2-ethoxyphenyl) benzamide, ML382, as a potent and selective positive allosteric modulator of MrgX1.

There is a need for alternate treatments of pain including chronic pain. In addition, there is a need for compounds that are potentiators of the hMrgX1 receptor.

Accordingly, in one embodiment, the present invention provides a compound of Formula I:

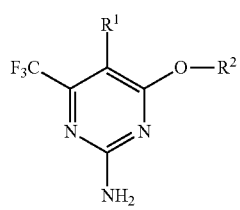

Formula I wherein $R^1$ is hydrogen or methyl; and $R^2$ is:

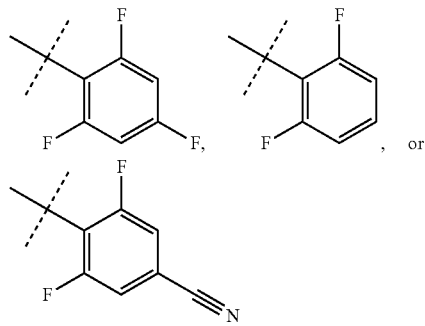

or a pharmaceutically acceptable salt thereof.

In an embodiment, $R^1$ is hydrogen.
In an embodiment, $R^1$ is methyl.
In an embodiment, $R^2$ is:

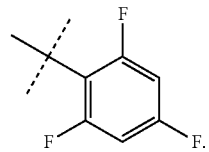

In an embodiment, $R^2$ is:

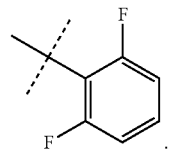

In an embodiment, $R^2$ is:

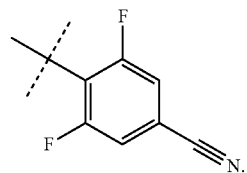

In a particular embodiment, the compound is:

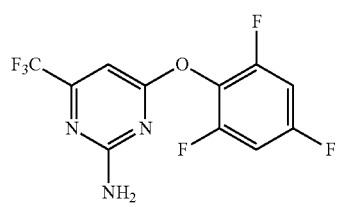

or a pharmaceutically acceptable salt thereof.

In a particular embodiment, the compound is:

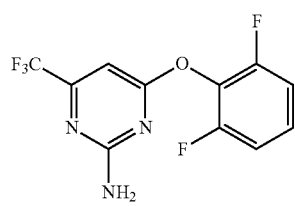 [SMILES: Nc1nc(Oc2c(F)cccc2F)cc(C(F)(F)F)n1]

or a pharmaceutically acceptable salt thereof.

In a particular embodiment, the compound is:

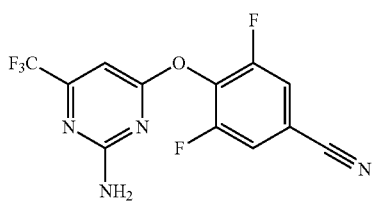 [SMILES: N#Cc1cc(F)c(Oc2cc(C(F)(F)F)nc(N)n2)c(F)c1]

or a pharmaceutically acceptable salt thereof.
In a particular embodiment, the compound is:

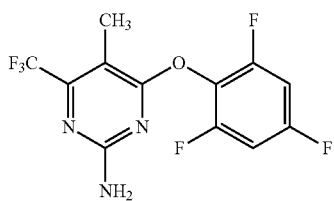

or a pharmaceutically acceptable salt thereof.
In a particular embodiment, the compound is:

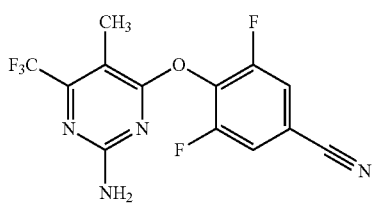

or a pharmaceutically acceptable salt thereof.
In a particular embodiment, the compound is:

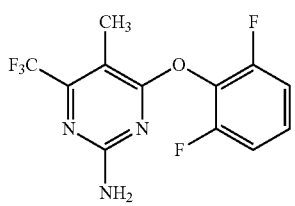

or a pharmaceutically acceptable salt thereof.

In an embodiment, the present invention also provides a method of treating pain in a patient in need of such treatment, comprising administering to the patient an effective amount of a compound of Formula I, or a pharmaceutically acceptable salt thereof. In an embodiment, the present invention further provides a method of treating chronic pain in a patient in need of such treatment, comprising administering to the patient an effective amount of a compound of Formula I, or a pharmaceutically acceptable salt thereof. In an embodiment, the present invention further provides a method of treating chronic lower back pain in a patient in need of such treatment, comprising administering to the patient an effective amount of a compound of Formula I, or a pharmaceutically acceptable salt thereof. In an embodiment, the present invention further provides a method of treating diabetic peripheral neuropathic pain in a patient in need of such treatment, comprising administering to the patient an effective amount of a compound of Formula I, or a pharmaceutically acceptable salt thereof. In an embodiment, the present invention further provides a method of treating osteoarthritis pain in a patient in need of such treatment, comprising administering to the patient an effective amount of a compound of Formula I, or a pharmaceutically acceptable salt thereof.

In an embodiment, the present invention further provides a compound of Formula I, or a pharmaceutically acceptable salt thereof for use in therapy. In an embodiment, the present invention provides a compound of Formula I, or a pharmaceutically acceptable salt thereof for use in treating pain. In an embodiment, the present invention provides a compound of Formula I, or a pharmaceutically acceptable salt thereof, for use in treating chronic pain.

In an embodiment, the present invention also provides the use of a compound of Formula I, or a pharmaceutically acceptable salt thereof, for the manufacture of a medicament for treating pain. In an embodiment, the present invention provides the use of a compound of Formula I, or a pharmaceutically acceptable salt thereof, for the manufacture of a medicament for treating chronic pain.

In an embodiment, the present invention further provides a pharmaceutical composition, comprising a compound of Formula I, or a pharmaceutically acceptable salt thereof, with one or more pharmaceutically acceptable carriers, diluents, or excipients. In an embodiment, the present invention further provides a process for preparing a pharmaceutical composition, comprising admixing a compound of Formula I, or a pharmaceutically acceptable salt thereof, with one or more pharmaceutically acceptable carriers, diluents, or excipients. In an embodiment, the present invention also encompasses novel intermediates and processes for the synthesis of compounds of Formula I.

As used herein, the terms "treating", "treatment", or "to treat" includes restraining, slowing, stopping, or reversing the progression or severity of an existing symptom or disorder.

As used herein, the term "patient" refers to a mammal, in particular a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are formulated as pharmaceutical compositions administered by any route which makes the compound bioavailable. Most preferably, such compositions are for oral administration. Such pharmaceutical compositions and processes for preparing same are well known in the art (See, e.g., Remington: The Science and Practice of Pharmacy, L. V. Allen, Editor, $22^{nd}$ Edition, Pharmaceutical Press, 2012).

Certain intermediates described in the following preparations may contain one or more nitrogen protecting groups. It is understood that protecting groups may be varied as appreciated by one of skill in the art depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

A pharmaceutically acceptable salt of a compound of the invention can be formed, for example, by reaction of an appropriate free base of a compound of the invention, an appropriate pharmaceutically acceptable acid in a suitable solvent such as diethyl ether under standard conditions well known in the art. Additionally, the formation of such pharmaceutically acceptable salts can occur simultaneously upon deprotection of a nitrogen protecting group. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," Journal of Pharmaceutical Sciences, 66: 1-19, (1977).

Certain abbreviations are defined as follows: "ACN" refers to acetonitrile; "BAM8-22" refers to bovine adrenal medulla peptide 8-22; "Cat. #" refers to catalog number; "CRC" refers to concentration-response curve; "DMEM" refers to Dulbecco's modified eagle media; "DMSO" refers to dimethyl sulfoxide; "DPBS" refers to Dulbecco's phosphate-buffered saline; "$EC_{50}$" refers to the effective concentration of an agent that gives a half-maximal response between baseline and maximum after a specified exposure time; "EDTA" refers to ethylenediaminetetraacetic acid; "ESMS" refers to Electrospray Mass Spectrometry; "FBS" refers to fetal bovine serum; "g" refers to gram or grams; "h" refers to hour or hours; "HEC" refers to hydroxyethylcellulose; "HEK293" refers to human embryonic kidney 293 cell or cells; "HEPES" refers to (4-(2-hydroxyethyl)-1-piperazineethanesulfonic acid); "hMrgX1" refers to human MrgX1 receptor; "HTRF" refers to homogeneous time resolved fluorescence; "IP 1" refers to inositol monophosphate; "$K_{p,uu}$" refers to unbound brain-to-plasma partition coefficient; "LC-ESMS" refers to refers to Liquid Chromatography Electrospray Mass Spectrometry; "min" refers to minute or minutes; "mL" refers to milliliter or milliliters; "Me" refers to methyl; "mol" refers to mole or moles; "mmol" refers to millimole or millimoles; "nm" refers to nanometer or nanometers; "nmol" refers to nanomoles; "m/z" refers to mass-to-charge ration for mass spectroscopy; "n," when in the context of biological data, refers to the number of runs or number of times tested; "PBS" refers to phosphate-buffered saline; "rpm" refers to revolutions per minute or minutes; "SD" refers to standard deviation; "SEM" refers to standard error of the mean; "U/mL" refers to units per milliliter.

General Chemistry

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. The following schemes, preparations, examples, and assays further illustrate the invention, but should not be construed to limit the scope of the invention in any way.

Scheme 1

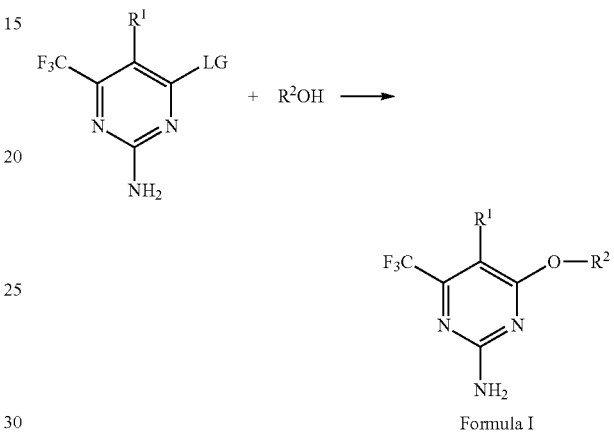

LG = e.g., Cl, Br, I, triflate, mesylate, tosylate

Scheme 1 depicts a general preparation of compounds of Formula I ($R^1$=H or $CH_3$; $R^2$=2,6-difluorophenyl, 2,4,6-trifluorophenyl, or 4-cyano-2,6-difluorophenyl) via nucleophilic aromatic substitution, as is well known to a person of ordinary skill in the art. Additionally, compounds of Formula I may be prepared via transition-metal (e.g., copper-, nickel-, or palladium-mediated) cross-coupling or Ullmann-type reactions as is well described in the art.

The 2-amino-6-trifluoromethyl-5-substituted pyrimidine starting material with an appropriate leaving group (LG) at the 4-position (e.g., LG=Cl, Br, I, triflate, mesylate, tosylate) may be purchased commercially. Alternatively, a person of ordinary skill in the art will recognize that the appropriate starting material may be prepared under a variety of techniques well documented in the art, such as dehydrative cyclization of guanidine with an appropriate 5-substituted 4,4,4-trifluoro-2-methyl-3-oxo-butanoic acid ester ($R^1$=H, $CH_3$) under basic conditions. Conversion of the subsequent cyclized 2-amino-6-trifluoromethyl-4-hydroxy-5-substituted pyrimidine to an appropriate LG at the 4-position is well recognized to a person of ordinary skill in the art.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT® HP1100 liquid chromatography system. Electrospray mass spectrometry measurements are performed on a Mass Selective Detector quadrupole mass spectrometer interfaced to the HP1100 HPLC. LC-MS conditions (low pH): column: PHE-NOMENEX® GEMINI® NX C18 2.1×50 mm 3.0 μm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 μm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH$_4$HCO$_3$ pH 9; Solvent B: ACN; wavelength: 214 nm.

Preparation 1

4-(4-Bromo-2,6-difluoro-phenoxy)-6-(trifluoromethyl)pyrimidin-2-amine

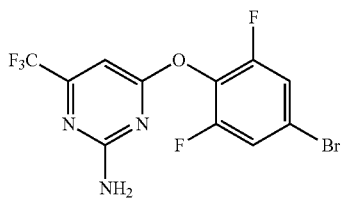 [SMILES: Nc1nc(Oc2c(F)cc(Br)cc2F)cc(C(F)(F)F)n1]

Combine 2-amino-4-chloro-6-(trifluoromethyl)pyrimidine (500 mg, 2.4 mmol) and 4-bromo-2,6-difluorophenol (616 mg, 2.9 mmol) to a microwave vial and add ACN (10 mL). Add potassium carbonate (665 mg, 4.8 mmol), seal the vial, and heat at 160° C. for 1 h in a microwave reactor. Cool the reaction mixture, dilute with water, and extract three times with ethyl acetate. Combine the organic extracts and dry over sodium sulfate. Filter and evaporate the resulting filtrate under reduced pressure. Purify the resulting residue by flash chromatography over silica gel, using a gradient of 5-100% ethyl acetate in hexanes, to afford the title compound (789 mg, 89% yield), after solvent evaporation of the desired chromatographic fractions. ESMS (m/z, $^{79}$Br/$^{81}$Br): 370/372 [M+H].

Preparation 2

2-Amino-5-methyl-6-(trifluoromethyl)pyrimidin-4-ol

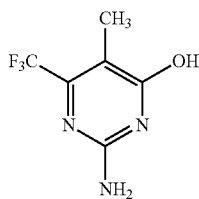

Add a 25% solution of sodium methoxide in methanol (5.5 mL, 24 mmol) to a solution of ethyl 4,4,4-trifluoro-2-methyl-3-oxo-butanoate (4 g, 20 mmol) and guanidine (1.2 g, 20 mmol) in methanol (100 mL). Stir for 23 h at room temperature. Evaporate the reaction mixture under reduced pressure. Dissolve the resulting white solid in water (20 mL) and acidify with acetic acid (2 mL). Collect the resulting product by vacuum filtration, wash twice with water, and dry the resulting filter cake under vacuum to obtain the title compound (2.3 g, 60% yield) as a white solid. ESMS (m/z): 194 [M+H].

Preparation 3

4-Chloro-5-methyl-6-(trifluoromethyl)pyrimidin-2-amine

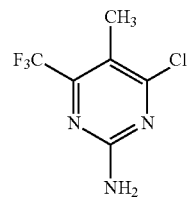

In a microwave vial, add phosphoryl chloride (5.5 mL, 59 mmol) to 2-amino-5-methyl-6-(trifluoromethyl)pyrimidin-4-ol (2.3 g, 11.9 mmol). Heat the reaction mixture at 110° C. for 30 min in a microwave reactor. Pour the reaction mixture onto ice, basify with 5 M aqueous NaOH (50 mL), and extract with ethyl acetate (100 mL). Dry the combined extracts over sodium sulfate, filter, and evaporate the resulting filtrate under reduced pressure. Dissolve the resulting residue in dichloromethane and purify by flash chromatography over silica gel, eluting with 10-25% ethyl acetate in hexanes, to obtain the title compound (813 mg, 32% yield) as a white solid, after evaporation of the desired chromatographic fractions. ESMS (m/z, $^{35}$Cl/$^{37}$Cl): 212/214 [M+H].

Preparation 4

4-Chloro-5-iodo-6-(trifluoromethyl)pyrimidin-2-amine

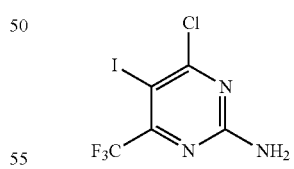

Combine 4-chloro-6-(trifluoromethyl)pyrimidin-2-amine (5 g, 25.2 mmol) in acetic acid (300 mL) with N-iodosuccinimide (32.0 g, 138 mmol) at 0° C. Heat and stir the resulting mixture at 70° C. overnight. Cool the reaction and quench with water (120 mL). Extract with ethyl acetate (100 mL×2). Wash the combined organic layers with brine (50 mL×2), dry over Na$_2$SO$_4$, filter, and concentrate under reduced pressure. Purify the crude product by flash chromatography to afford 4.8 g (53% yield) of the title product as a yellow solid. ES/MS m/z 324[M+H]$^+$

Preparation 5

4-((2-Amino-5-iodo-6-(trifluoromethyl)pyrimidin-4-yl)oxy)-3,5-difluorobenzonitrile

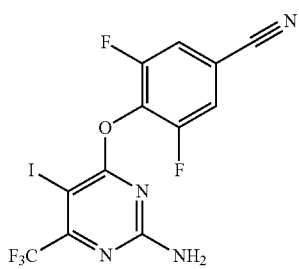 [SMILES: N#Cc1cc(F)c(Oc2nc(N)nc(C(F)(F)F)c2I)c(F)c1]

Combine 4-chloro-5-iodo-6-(trifluoromethyl)pyrimidin-2-amine (2.5 g, 7.0 mmol, 90 mass %) and 3,5-difluoro-4-hydroxy-benzonitrile (1.33 g, 8.49 mmol) in DMF (35 mL) and add potassium carbonate (2.88 g, 20.8 mmol). Heat the reaction mixture at 90° C. for 3 h. Cool the reaction mixture and quench with water (100 mL). Extract with ethyl acetate (60 mL×2) and wash the combined organic layers with brine (50 mL×2), dry over $Na_2SO_4$, filter, and concentrate under reduced pressure. Purify the crude product with flash chromatography to afford 2.6 g (76% yield) of the title product as a white solid. ES/MS m/z 443[M+H]$^+$

Example 1

4-(2,6-Difluorophenoxy)-6-(trifluoromethyl)pyrimidin-2-amine

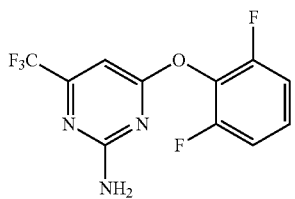

In a microwave vial, add potassium tert-butoxide (270 mg, 2.4 mmol) to a solution of 2-amino-4-chloro-6-(trifluoromethyl)pyrimidine (395 mg, 2.0 mmol) and 2,6-difluorophenol (289 mg, 2.2 mmol) in ACN (8.0 mL). Heat the reaction mixture at 120° C. for 30 min in a microwave reactor. Filter the reaction mixture through diatomaceous earth and evaporate the filtrate under reduced pressure. Dissolve the resulting residue in dichloromethane containing a small amount of methanol and purify the mixture by flash chromatography over silica gel, eluting with a gradient of 5-20% ethyl acetate in hexanes, to obtain the title compound (512 mg, 88% yield) as a white crystalline solid, after solvent evaporation of the desired chromatographic fractions. ESMS (m/z): 292 [M+H].

Example 2

4-(2,4,6-Trifluorophenoxy)-6-(trifluoromethyl)pyrimidin-2-amine

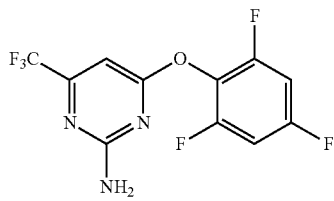 [SMILES: Nc1nc(Oc2c(F)cc(F)cc2F)cc(C(F)(F)F)n1]

In a 500-mL round-bottom flask, add potassium carbonate (26.9 g, 194.7 mmol) to a solution of 2-amino-4-chloro-6-(trifluoromethyl)pyrimidine (19.55 g, 97 mmol) and 2,4,6-trifluorophenol (15.2 g, 97.5 mmol) in N,N-dimethylformamide (200 mL). Heat the reaction mixture at 80° C. for 16 h. Quench the reaction mixture with water (500 mL) and extract with ethyl acetate (2×500 mL). Wash the combined organic extracts with saturated aqueous NaCl (2×800 mL), dry over sodium sulfate, filter, and concentrate the resulting filtrate under reduced pressure. Purify the resulting residue by flash chromatography over silica gel, eluting with a gradient of 0-37% ethyl acetate in petroleum ether, to obtain the title compound (15.9 g, 53% yield) as a yellow solid, after evaporation of the desired chromatographic fractions. ESMS (m/z): 310 [M+H].

Example 3

4-[2-Amino-6-(trifluoromethyl)pyrimidin-4-yl]oxy-3,5-difluoro-benzonitrile

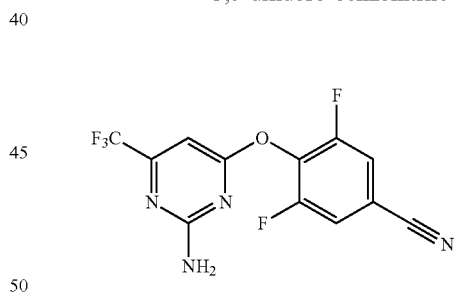

Combine 4-(4-bromo-2,6-difluoro-phenoxy)-6-(trifluoromethyl)pyrimidin-2-amine (300 mg, 0.8 mmol), zinc cyanide (291 mg, 2.4 mmol), tetrakis(triphenylphosphine)palladium (0) (188 mg, 162 nmol) in a microwave vial and add N,N-dimethylformamide (6 mL). Seal the vial and heat to 100° C. overnight in a heating block. Cool the reaction, dilute with water, and extract three times with ethyl acetate. Combine the organic extracts and dry over sodium sulfate. Filter and evaporate the resulting filtrate under reduced pressure. Purify the resulting residue by flash chromatography over silica gel, using a gradient of 5-100% ethyl acetate in hexanes, to afford the title compound (200 mg, 78% yield), after solvent evaporation of the desired chromatographic fractions. ESMS (m/z): 317 [M+H].

Example 4

5-Methyl-4-(trifluoromethyl)-6-(2,4,6-trifluorophenoxy)pyrimidin-2-amine

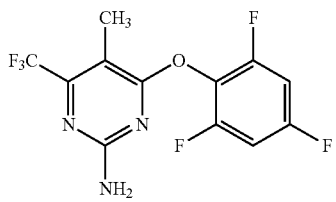

In a microwave vial, add potassium tert-butoxide (69 mg, 0.6 mmol) to a solution of 4-chloro-5-methyl-6-(trifluoromethyl)pyrimidin-2-amine (106 mg, 0.5 mmol) and 2,4,6-trifluorophenol (84 mg, 0.6 mmol) in ACN (2.0 mL). Heat the reaction mixture at 120° C. for 30 min in a microwave reactor. Filter the reaction mixture and evaporate the resulting filtrate under a stream of air. Dissolve the resulting residue in 1:1 dichloromethane/methanol and purify by flash chromatography over silica gel, eluting with 5-10% ethyl acetate/hexanes, to obtain the title compound (154 mg, 95% yield) as an off-white solid, after solvent evaporation of the desired chromatographic fractions.

ESMS (m/z): 324 [M+H].

Example 5

4-[2-Amino-5-methyl-6-(trifluoromethyl)pyrimidin-4-yl]oxy-3,5-difluoro-benzonitrile

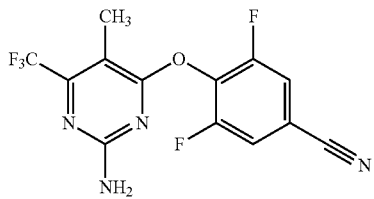

Combine 4-((2-amino-5-iodo-6-(trifluoromethyl)pyrimidin-4-yl)oxy)-3,5-difluorobenzonitrile (1.2 g, 2.4 mmol, 90% purity) and trimethylboroxine (2.5 g, 10 mmol, 50% mass) in 1,4-dioxane (25 mL) and then add cesium carbonate (2.4 g, 7.4 mmol) and tetrakis(triphenylphosphine)palladium (0) (580 mg, 0.486855 mmol) and heat the reaction to 120° C. for 2 h under nitrogen. Cool the reaction mixture and quench with water (50 mL) and extract with ethyl acetate (50 mL×2). Combine the organic layers and wash with brine (30 mL×2). Dry the organic layer over sodium sulfate, filter, and concentrate under reduced pressure. Purify the crude product by flash silica gel chromatography initially and then further purify by prep-HPLC (Instrument DD, Method Column Xtimate C18 150*40 mm*10 um, Condition water (10 mM NH$_4$HCO$_3$)-ACN Begin B 50%, End B 80%, with a 10 minute gradient time (min) 10,100% B, Hold Time (min) 2, Flow Rate 60 mL/min). The afforded flows are combined, concentrated to remove most of CH$_3$CN and then lyophilized to afford 481 mg (60% yield) of the title compound as a white solid. ES/MS (m/z): 331 (M+H).

Example 6

4-(2,6-difluorophenoxy)-5-methyl-6-(trifluoromethyl)pyrimidin-2-amine

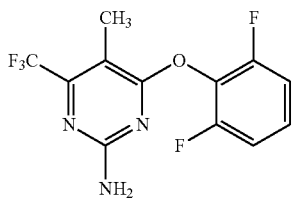 [SMILES: Cc1c(Oc2c(F)cccc2F)nc(N)nc1C(F)(F)F]

In a microwave vial, add potassium tert-butoxide (69 mg, 0.6 mmol) to a solution of 4-chloro-5-methyl-6-(trifluoromethyl)pyrimidin-2-amine (106 mg, 0.5 mmol) and 2,6-difluorophenol (72 mg, 0.6 mmol) in acetonitrile (2.0 mL). Heat the reaction mixture at 120° C. for 30 min in a microwave reactor. Filter the reaction mixture and evaporate the resulting filtrate under a stream of air. The crude product is purified by reverse phase chromatography to obtain the title compound (124 mg, 81% yield) as a white solid. ESMS (m/z): 306 [M+H].

IP1 Cellular Assay for EC$_{50}$ Determination Against hMrgX1 by HTRF

Cell plating: HEK293 cells stably expressing the recombinant human MrgX1 receptor are expanded in culture flasks (Corning, T150), using growth media containing DMEM with glutamine (GIBCO™, Cat. #11960-044) supplemented with 10% heat-inactivated FBS (HyClone™, Cat. #CH30073), 1% penicillin/streptomycin (HyClone™, Cat. #SV30010; 10,000 U/mL penicillin; 10,000 μg/mL streptomycin in 0.85% NaCl), 20 mM HEPES (GIBCO™, Cat. #15530122) and 0.3 mg/mL G418 (GIBCO™, Cat. #11811031). When cell monolayers achieve a level of 80-90% confluence, monolayers are washed once with 10 mL of DPBS (HyClone™, Cat. #14190-144), dissociated using TrypLE™ Express enzyme cell dissociation media (GIBCO™, Cat. #12605-010), and diluted by addition of 10 mL DPBS. Dissociated cells are transferred to a sterile 50 mL conical tube, pelleted by centrifugation at 300×g to remove the growth and dissociation media, and diluted to 1M cells/mL into DMEM for plating.

IP1 Potency and Efficacy Determination: Test compounds are dissolved in DMSO to a concentration of 10 mM and serially diluted in DMSO to obtain a 10-point concentration response stock dilution plate. Growth media is removed from the cell plate, and the stock 10-point dilution plate is diluted into media and stamped into the cell plate at a concentration 2× higher than the final test concentration of 30 μM maximum. The endogenous agonist BAMS-22 (Tocris-BioScience® Cat. #1763) is diluted to the EC$_{15}$, determined independently at a minimum of n=3, into the cell plate and incubated at room temperature for 120 min. Subsequently, half the volume each of anti-IP1 cryptate and d2-labeled IP1 in lysis buffer, supplied with the IP-One Gq Kit (CisBio Cat. #62IPAPEC) are added to the cell plate to initiate cell lysis, and incubated for 60 min at room temperature in the dark. At that point, fluorescence is determined at 620 and 665 nm (~100 μs following laser excitation).

Data Analysis: Fluorescent ratios are determined as the ratio of the fluorescence emission at 620 nm over 665 nm and converted to IP1 concentration, using the IP1 standard curve generated in a separate plate, following the manufacturer's instructions. The IP1 concentration is then plotted as a function of compound concentration. Potentiator potency ($EC_{50}$) is defined as the compound concentration, in the presence of the $EC_{15}$ of the endogenous agonist BAMS-22, resulting in 50% of the increase in IP1 concentration achieved by a saturating concentration of BAMS-22, and is determined by using Genedata software (GeneData AG, Basel Switzerland) fitting the following equation to the 10-point CRC, where y is the IP1 concentration determined for a given compound concentration, [L] denotes the concentration of test compound and Max is the maximum increase achieved by a saturating concentration of BAMS-22:

$$Y = Max*[L]/(EC_{50}+[L])$$

$EC_{50}$ values are reported as the geometric mean in nM (SEM, n).

TABLE 1

Relative $EC_{50}$ against hMrgX1 IP-1 for the compounds of Examples 1-6

| Example | Relative $EC_{50}$ (SEM, n) (nM) | Max (Mean ± SEM) (nM) |
|---|---|---|
| 1 | 72 (30, 4) | 98 ± 5.3, n = 4 |
| 2 | 61 (26, 4) | 109 ± 9.2, n = 4 |
| 3 | 104 (26, 13) | 109 ± 2.5, n = 13 |
| 4 | 40 (8, 5) | 125 ± 7.9, n = 5 |
| 5 | 82, n = 1 | 120 |
| 6 | 38 (3, 3) | 103 ± 1.9, n = 3 |

Table 1 shows the relative $EC_{50}$ and the maximum stimulation achieved in the assay for the compounds of Examples 1 to 6, indicating these compounds are potentiators of hMrgX1.

In Vivo Determination of $K_{p,uu,brain}$ in Mice

Unbound brain-to-plasma partition coefficient ($K_{p,uu,brain}$) is one of the key pharmacokinetic parameter for evaluating a compound's ability to cross the blood-brain barrier (BBB). It is typically measured in pre-clinical species using the following methodology. $K_{p,uu,brain}$ values indicate the fraction of free drug in plasma that partitions across the BBB.

Subjects: The subjects for these studies are 12 male C57Bl/6 mice (Envigo, Indianapolis, IN, USA) between 8-10 weeks old at time of test. Mice are housed in groups of 4 in high density plastic home cages. Food and water is available ad libitum. The rooms are maintained at 73° F. with 30-70% relative humidity and kept on a light/dark cycle of 0600-1800 h.

Agent: The compound of Example 2 is prepared at 0.3, 1, and 3 mg/ml in the 1% HEC, 0.25% TWEEN®80, 0.05% DOWSIL™ vehicle in water. Prepared compound is sonicated in water bath for 30 min until a suspension is formed. Mice are dosed at 10 ml/kg for a respective 3, 10 or 30 mg/kg dose.

Dosing and Tissue Collection: For this experiment, four mice per dosing group receive oral dosing of either: 3, 10, or 30 mg/kg of the compound of Example 2. Mice are euthanized at 2 h post-dosing via $CO_2$ asphyxiation, plasma samples are collected via cardia puncture, and mouse brains removed, weighed, and frozen on dry ice. Blood samples are stored in EDTA tubes on wet ice and centrifuged at 15 k rpm for 10 min. Plasma is collected, plated in a 96-well plate, and frozen at −80° C.

Pharmacokinetic sampling: Plasma and brain samples obtained are analyzed for Example 2 using an LC-MS/MS method (Q2 Solutions, Indianapolis, IN, USA). Plasma samples are extracted using protein precipitation. The lower limit of quantification is 25 ng/mL, and the upper limit of quantification is 5000 ng/mL. Brain samples are homogenized, and the analyte is extracted using protein precipitation. The lower limit of quantification is 4 ng/g and the upper limit of quantification is 200000 ng/g.

Determination of plasma and brain protein binding: Mouse plasma and brain homogenate protein binding is determined in vitro using equilibrium dialysis, as described elsewhere [Zamek-Gliszczynski et al., J Pharm Sci, 101: 1932-1940, 2012]. The results are reported as fraction unbound in plasma ($f_{u,plasma}$) and brain ($f_{u,brain}$) which are then utilized to calculate $K_{p,uu,brain}$ as described below. Mouse $f_{u,plasma}$ and $f_{u,brain}$ of Example 2 are determined to be 0.0421 and 0.0181, respectively.

Analysis and Results: $K_{p,uu,brain}$ is calculated for each time point from the expression below where individual components are derived from a combination of in vitro and in vivo measurements carried out as described above:

$$K_{p,uu,brain} = \frac{C_{u,brain}}{C_{u,plasma}} = \frac{C_{total,brain}}{C_{total,plasma}} \cdot \frac{f_{u,brain}}{f_{u,plasma}}$$

where $C_{total,brain}$, $C_{u,brain}$, $C_{total,plasma}$, and $C_{u,plasma}$ are total and unbound brain and plasma concentrations, and $f_{u,brain}$ and $f_{u,plasma}$ are fractions unbound in brain and plasma, respectively.

TABLE 2

Plasma and brain concentrations of Example 2 post 3, 10, and 30 mg/kg oral dose in mouse.

| Time point (Hours) | Dose Group (mg/kg) | Total brain conc. ($C_{total,brain}$) (nM) ± SD | Total plasma conc. ($C_{total,plasma}$) (nM) ± SD | Unbound brain conc. ($C_{u,brain}$) (nM)* ± SD | Unbound plasma conc. ($C_{u,plasma}$) (nM)^ ± SD | $K_{p,uu,brain}$ |
|---|---|---|---|---|---|---|
| 2 | 3 | 972 ± 353 | 809 ± 140 | 17.6 ± 6.39 | 34.1 ± 5.94 | 0.506 ± 0.107 |
| 2 | 10 | 3900 ± 1800 | 2770 ± 651 | 55.4 ± 32.5 | 117 ± 27.4 | 0.586 ± 0.116 |
| 2 | 30 | 13700 ± 4200 | 9700 ± 2410 | 248 ± 75.9 | 409 ± 101 | 0.601 ± .0553 |

*Using mouse $f_{u,brain}$ value of 0.0181 and ^mouse $f_{u,plasma}$ value of 0.0421, as described above.

The unbound plasma concentration and unbound brain concentration show dose related increases in both plasma and brain indicating the compound of Example 2 crosses the blood brain barrier and has central penetrance at 2 h post-oral administration in mice. There appears to be dose proportionality in plasma & brain exposure across the dose groups. Mean unbound brain to unbound plasma ratio (Kp, uu-brain) for the compound of Example 2 ranges from 0.506±0.1 to 0.601±0.0553 (mean±SD, n=4 per group); suggesting that an active transport mechanism is not operative in brain tissue in mouse.

We claim:

1. A compound of formula:

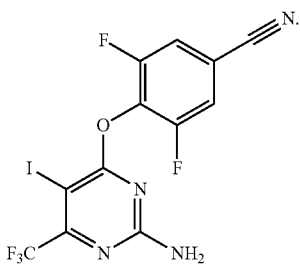 [SMILES: N#Cc1cc(F)c(Oc2nc(N)nc(C(F)(F)F)c2I)c(F)c1]

2. A method for preparing a compound of formula:

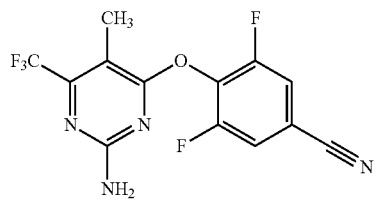

comprising combining the compound of claim 1 with trimethylboroxine in 1,4-dioxane, cesium carbonate, and tetrakis(triphenylphosphine)palladium(0) in a reaction.

3. A method for preparing the compound of claim 1, comprising combining a compound of formula:

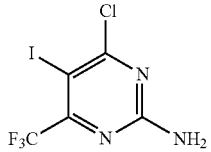

with 3,5-difluoro-4-hydroxybenzonitrile in a reaction.

4. A method for preparing a compound of a formula

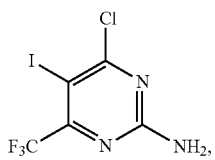

comprising combining 4-chloro-6-(trifluoromethyl)pyrimidin-2-amine in an acid with N-iodosuccinimide in a reaction.

5. The method of claim 4, wherein the acid is acetic acid.

* * * * *